(12) United States Patent
Jastrzebski et al.

(10) Patent No.: US 10,905,601 B2
(45) Date of Patent: Feb. 2, 2021

(54) WEARABLE SENSOR ENCLOSURE

(71) Applicant: Verily Life Sciences LLC, South San Francisco, CA (US)

(72) Inventors: Michael Jastrzebski, Newark, CA (US); Kristin Size, Waltham, MA (US); David He, San Mateo, CA (US); Harry Xiao, San Mateo, CA (US); Linden Evans, San Francisco, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 0 days.

(21) Appl. No.: 16/383,340

(22) Filed: Apr. 12, 2019

(65) Prior Publication Data

US 2020/0323701 A1 Oct. 15, 2020

(51) Int. Cl.
*A61F 13/42* (2006.01)

(52) U.S. Cl.
CPC ........ *A61F 13/42* (2013.01); *A61F 2013/422* (2013.01); *A61F 2013/424* (2013.01)

(58) Field of Classification Search
CPC ...................................................... A61F 13/42
See application file for complete search history.

(56) References Cited

U.S. PATENT DOCUMENTS

| | | | |
|---|---|---|---|
| 8,431,766 B1 | 4/2013 | Lonero | |
| 9,880,052 B2 * | 1/2018 | Dumont | G01J 1/0271 |
| 10,039,675 B1 * | 8/2018 | Cai | A45F 5/02 |
| D828,186 S | 9/2018 | Barnes et al. | |
| 10,226,187 B2 * | 3/2019 | Al-Ali | A61B 5/113 |
| 2004/0207530 A1 * | 10/2004 | Nielsen | A61F 13/42 340/604 |
| 2008/0287751 A1 * | 11/2008 | Stivoric | A61B 5/1118 600/301 |
| 2011/0133103 A1 * | 6/2011 | Folkesson | G01J 1/50 250/474.1 |
| 2014/0090967 A1 | 4/2014 | Inagaki | |
| 2014/0203797 A1 | 7/2014 | Stivoric et al. | |
| 2014/0375297 A1 * | 12/2014 | Geiger | A61F 13/42 324/71.1 |
| 2015/0077261 A1 * | 3/2015 | Lineberry | A61F 13/42 340/604 |

(Continued)

OTHER PUBLICATIONS

Chinese Application No. 201921351428.5, "Notice of Decision to Grant", dated Jan. 23, 2020, 2 pages.

(Continued)

*Primary Examiner* — Jamel E Williams
(74) *Attorney, Agent, or Firm* — Kilpatrick Townsend & Stockton LLP

(57) ABSTRACT

Various examples of a wearable sensor enclosure are described. In an example, a wearable sensor enclosure is generally oval-shaped with rigid interior that protects one or more sensors or other electronic devices. The enclosure includes a proximal component and a distal component. The proximal component of the enclosure optionally includes one or more openings for light to pass through for detection by sensing electronic devices. The distal component includes a protrusion positioned in an interior of the distal component and a lip positioned in along the perimeter of the distal component such that the lip surrounds the protrusion.

20 Claims, 10 Drawing Sheets

(56) References Cited

U.S. PATENT DOCUMENTS

| | | | | |
|---|---|---|---|---|
| 2015/0157512 A1* | 6/2015 | Abir | ............... | A61B 5/08 |
| | | | | 340/573.5 |
| 2015/0223755 A1* | 8/2015 | Abir | ............... | A61B 5/4288 |
| | | | | 600/300 |
| 2015/0272481 A1* | 10/2015 | Glaser | ............... | G06F 19/3418 |
| | | | | 600/301 |
| 2016/0198995 A1* | 7/2016 | Yeung | ............... | A61B 5/1128 |
| | | | | 600/595 |
| 2016/0363479 A1* | 12/2016 | Dumont | ............... | G01J 1/0403 |
| 2017/0202484 A1* | 7/2017 | Al-Shaery | ............... | A61B 5/1112 |
| 2017/0252225 A1* | 9/2017 | Arizti | ............... | A61F 13/49 |
| 2018/0325743 A1* | 11/2018 | Ho | ............... | A61B 5/6808 |
| 2020/0060886 A1* | 2/2020 | Arizti | ............... | A61B 5/0077 |

OTHER PUBLICATIONS

Chinese Application No. 201930547814.0 , "Notice of Decision to Grant", dated Mar. 20, 2020, 4 pages.
Chinese Application No. 201930547814.0 , "Office Action", dated Jan. 21, 2020, 1 page.
International Application No. PCT/US2020/027606, International Search Report and Written Opinion, dated Jun. 29, 2020, 8 pages.
U.S. Appl. No. 29/687,437, Notice of Allowance, dated Oct. 15, 2020, 6 pages.

* cited by examiner

WEARABLE SENSOR ENCLOSURE

FIELD

The present application generally relates to an enclosure, or a housing, for a sensor. In an example, the present application relates to a wearable sensor enclosure that can be worn on an absorbent article and can accommodate one or more electronic sensors such as accelerometers or optical sensors. A wearable sensor enclosure can accommodate electronic devices (e.g., sensors) and that can be attached or affixed to a wearer, e.g., to an item of clothing or an absorbent article such as a diaper. When attached, one or more sensors or related electronic devices in the wearable sensor enclosure can detect and analyze various measurements of the wearer.

BACKGROUND

Existing solutions for wearable sensor enclosures suffer from deficiencies. For example, existing solutions, which are typically designed for adult wearers, can be too large to use with children or infants. These solutions can include small parts which can break off, causing a hazard. Additionally, some existing solutions are shaped such that they can pose a safety or choking hazard in the event that the enclosure is placed in a child's mouth.

Additionally, existing solutions fail to indicate a preferred orientation of the wearable sensor enclosure. For example, if the orientation or alignment of the sensor is relevant for accuracy of the results, an incorrectly-positioned wearable sensor enclosure can result in the enclosed sensor detecting erroneous measurements.

Further, other housing solutions have sought to provide removable batteries. This can result in complexity of use and the battery compartment can provide an additional area for undesirable moisture ingress. Hence, new sensor enclosure solutions are needed.

SUMMARY

Various examples of a wearable sensor enclosure are described herein. In an example, a wearable sensor enclosure includes a proximal component and a distal component. The distal component is attached to the proximal component and has a perimeter. The distal component further includes a protrusion positioned in an interior of the distal component and an outer lip. The outer lip is positioned along the perimeter and surrounding the protrusion. The protrusion and the outer lip connect at a transition section that forms a concave curve. In some cases, the wearable sensor enclosure includes a superior end located opposite an inferior end. The superior end has a first width and the inferior end has a second width that is less than the first width.

In an aspect, the protrusion includes one or more of (i) a button area configured to activate an electronic switch disposed within the wearable sensor enclosure or (ii) a light source configured to emit light through the protrusion.

In an aspect, the concave curve includes a radius of 1-6 mm.

In an aspect, the wearable sensor enclosure is at least partially made from a flexible material and the proximal component includes an adhesive or attachment device for attaching to a diaper.

In an aspect, the proximal component includes an opening and the wearable sensor enclosure includes an interior sensor enclosure located between the distal component and the proximal component. The interior sensor enclosure includes one or more of: (i) a light source configured to emit light through the opening, or (ii) a light sensor configured to receive light through the opening.

In an aspect, the wearable sensor enclosure includes one or more of: (i) an accelerometer, (ii) a gyroscope, (iii) a light source, (iii) a light detector, (iv) a radio, (v) a power source, (vi) a temperature sensor, (vii) a moisture sensor, and (viii) a sound emitting device.

In an aspect, a wearable sensor enclosure includes a proximal component and a distal component attached to the proximal component and having a perimeter. The distal component includes a protrusion positioned in an interior of the distal component and an outer lip positioned along the perimeter and surrounding the protrusion. The protrusion and the outer lip connect at a transition section that forms a concave curve. The wearable sensor enclosure further includes a superior end located opposite an inferior end. The superior end has a first width and the inferior end has a second width. The second width is less than the first width.

In an aspect, the wearable sensor enclosure includes an orientation marking, the orientation marking indicating a preferred orientation of the wearable sensor enclosure.

In an aspect, the wearable sensor enclosure includes a sensor including a preferred orientation. The sensor is correctly oriented when the wearable sensor housing is oriented consistently with the preferred orientation indicated by the orientation marking.

In an aspect, the wearable sensor enclosure includes (i) a first distance from the perimeter and the protrusion as measured at the superior end and (ii) a second distance from the perimeter and the protrusion as measured at the inferior end. The first distance and the second distance are different.

In an aspect, the protrusion further includes one or more of (i) a button area configured to receive a push and activate an electronic switch disposed within the wearable sensor enclosure or (ii) a light source configured to emit light through the protrusion.

In an aspect, a wearable sensor enclosure includes a proximal component; and a distal component attached to the proximal component and having a perimeter. The distal component includes a protrusion positioned in an interior of the distal component and including a button area that is configured to activate an electronic switch within the wearable sensor enclosure. The distal component includes an outer lip positioned along the perimeter and surrounding the protrusion. The protrusion and the outer lip connect at a transition section that forms a concave curve.

In an aspect, the wearable sensor enclosure includes a superior end located opposite an inferior end. The superior end has a first width and the inferior end has a second width. The second width is less than the first width.

In an aspect, the wearable sensor enclosure includes an orientation marking on the protrusion, the orientation marking indicating a preferred orientation of the wearable sensor enclosure.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

Features, embodiments, and advantages of the present disclosure are better understood when the following Detailed Description is read with reference to the accompanying drawings.

DETAILED DESCRIPTION

Certain aspects of the present disclosure relate to a wearable sensor enclosure, or housing. In use, the wearable sensor enclosure can be placed on an absorbent article such as a diaper or otherwise attached to a wearer. When properly located, one or more sensors housed inside the wearable sensor enclosure can measure one or more parameters of the wearer. Non-limiting examples of suitable parameters that may be measured include movement, moisture (e.g., humidity or wetness), a presence of a volatile organic compound (VOC), light, sound, temperature, or other parameters. In one example, electronic devices installed in the wearable sensor enclosure can transmit the parameters to an external device. Non-limiting examples of suitable external devices include a monitor, an external computing server, a tablet, a cell phone, or any other device that can receive transmission from the one or more sensors housed inside the wearable sensor enclosure.

Wearable sensor enclosures can enable improved monitoring by enabling the placement of electronic sensors on an article of clothing or an absorbent article. For example, an accelerometer or gyroscope within the wearable sensor can detect movement of an infant and can detect, in conjunction with an external device, whether the infant is asleep, awake, or nursing. Wearable sensors can also measure parameters such as heartrate, breathing rate, or determine whether an infant's diaper needs to be changed. Wearable sensor enclosures facilitate such measurements while ensuring the sensors are protected and that the wearable sensor enclosure itself and its contents do not cause a hazard to the wearer.

Figure 1:
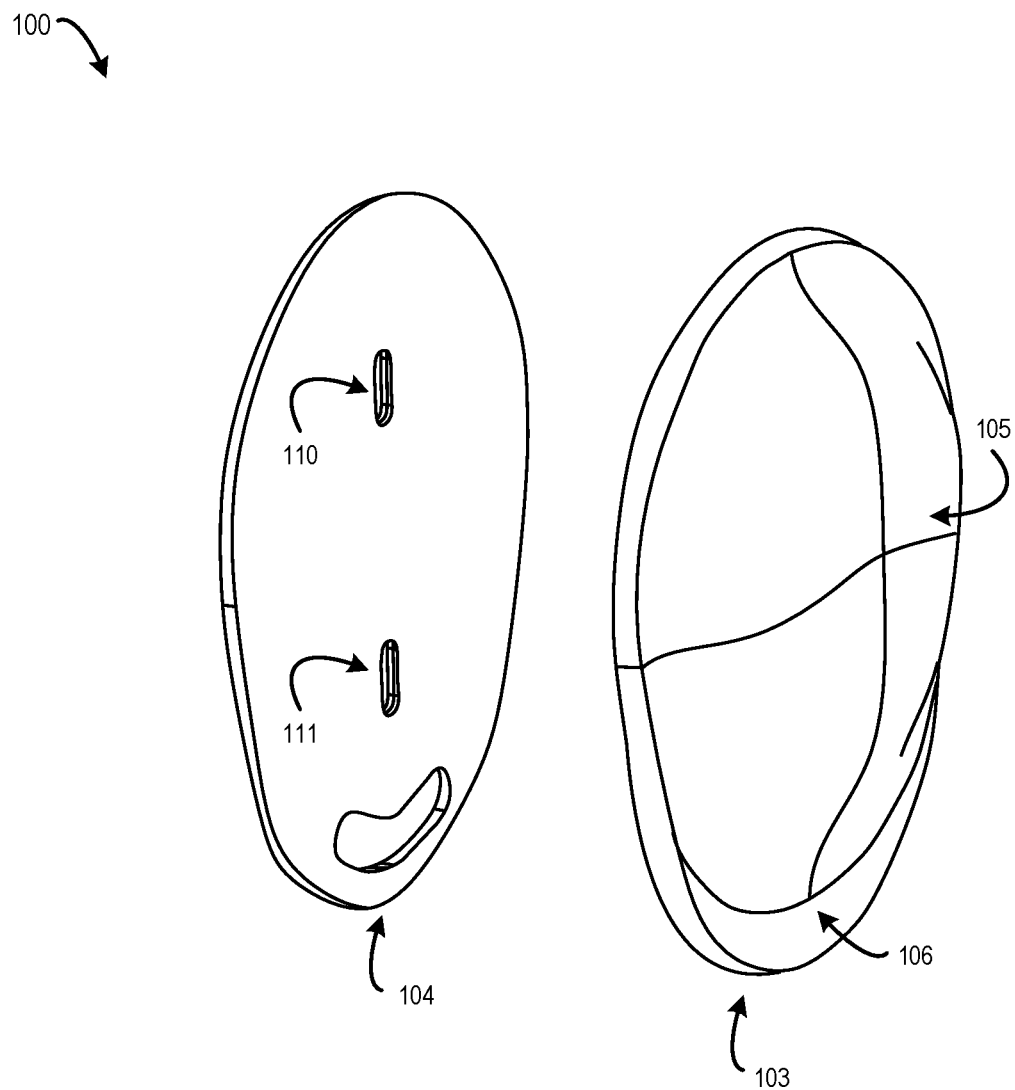
FIG. 1 depicts an exploded view of a wearable sensor enclosure, in accordance with an aspect of the present disclosure.

Turning now to the figures, FIG. 1 depicts wearable sensor enclosure 100, which includes a distal component 103 and a proximal component 104. The distal component 103, or lower housing, is generally the component that is oriented away from the wearer (or away from a diaper) while the sensor is in use. The distal component 103 is shown as having a first section, which may also be referred to as a protrusion 105, positioned in the interior of the distal component 103 with respect to a second section, which may be referred to as an outer lip 106. The protrusion can protrude upwards, defining an internal cavity on an under surface of the distal component 103. This internal cavity can facilitate room for an electronic circuit, one or more sensors, or any other electronic component to be placed on the interior of the wearable sensor enclosure 100. The distal component 103 can also include outer lip 106, that is positioned around a perimeter of the distal component 103. As shown, the outer lip 106 can generally be thinner than the protrusion 105. In this manner, the outer lip 106 creates a ridge, edge, or flange around at least one portion of the wearable sensor enclosure 100.

The proximal component 104, or upper housing, is generally oriented to face towards the wearer (or towards a diaper) while the sensor is in use. It can provide a base for the wearable sensor enclosure 100. In some examples, the lower surface of the proximal component 104 is planar or otherwise flat so that it lies flush with the wearer, the diaper, or other measured surface. The proximal component is also shown as having openings 110 and 111. Although two openings 110, 111 are illustrated, it should be understood that fewer or more openings may be provided. In an example, openings 110, 111 are cutouts. In another example, openings 110, 111 are transparent windows through which light can enter into or exit the wearable sensor enclosure 100.

In an exemplary use case, the wearable sensor enclosure 100 is placed on or affixed to an absorbent article such that the proximal component 104 is on the absorbent article and the distal component 103 is oriented away from a wearer of the absorbent article.

As discussed, in some cases, the wearable sensor enclosure 100 can indicate orientation as to aid with placing the wearable sensor enclosure 100 on an absorbent article or wearer in such a way that any sensors located within wearable sensor enclosure 100 are correctly aligned to enable an accurate sensor measurement to be taken. Because internal sensors are typically configured to be oriented in a particular direction, a lack of an orientation indicator can result in the wearable sensor enclosure, and therefore the internal sensors, being misaligned. As an example, the wearable sensor may detect wetness in an article or diaper by sensing change in color of a color change strip. In such cases, failure to properly align the wearable sensor over the color change strip can result in inaccurate sensor readings.

For example, the wearable sensor enclosure 100 can include one or more orientation markings (not depicted). In one example, the orientation marking can indicate a preferred orientation of the wearable sensor enclosure. The orientation markings may be positioned on the distal component 103, protrusion 105, or outer lip 106, on the proximal component 104, or any combination thereof. Non-limiting examples of orientation markings may include an arrow, a word, an animal, a shape, a letter of the alphabet, or any other marking that has a configuration or orientation that is easily detectable that it is right side up or upside down.

Figure 2:
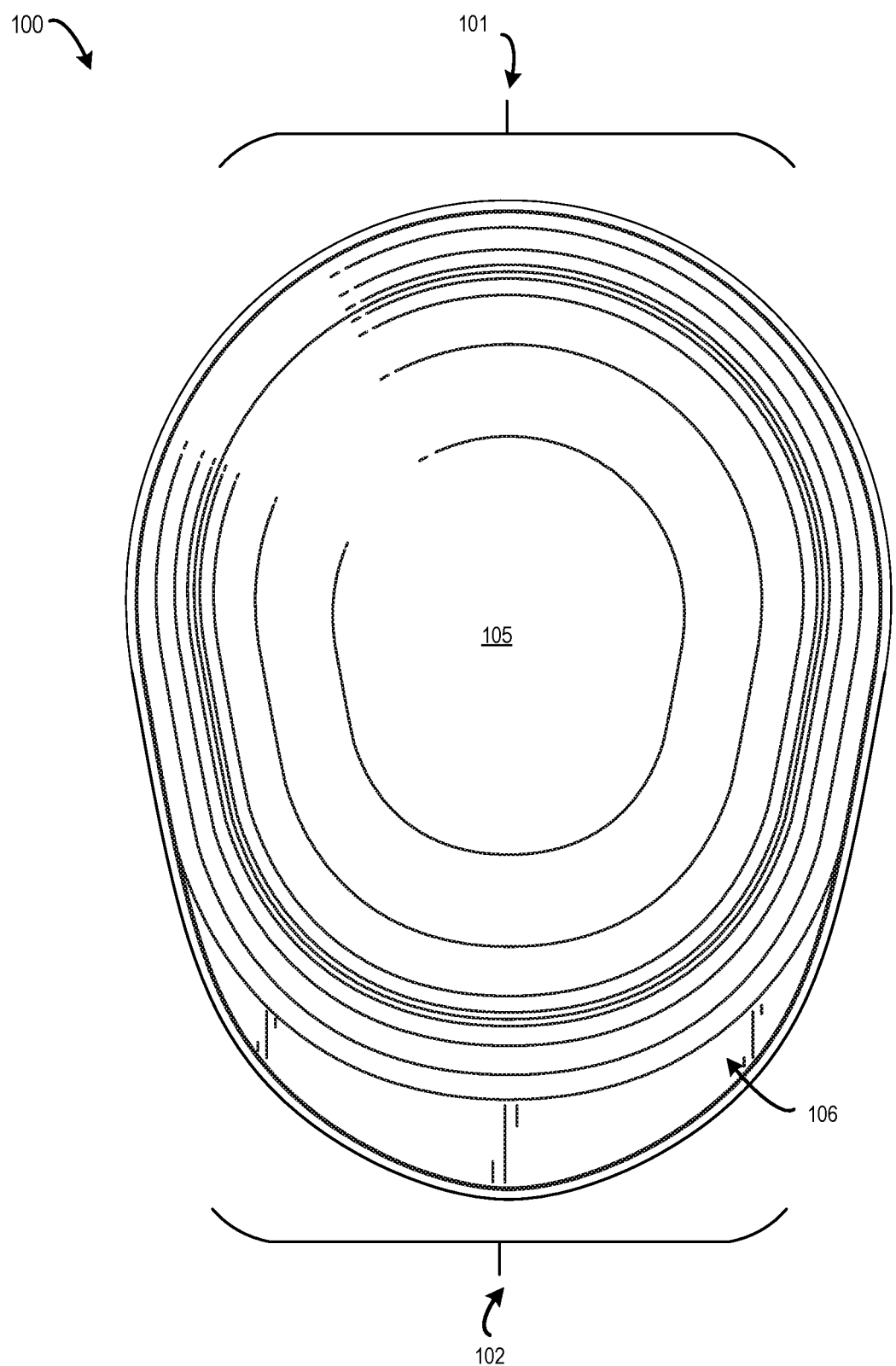
FIG. 2 depicts a top view of the wearable sensor enclosure of FIG. 1, in accordance with an aspect of the present disclosure.
Figure 3:
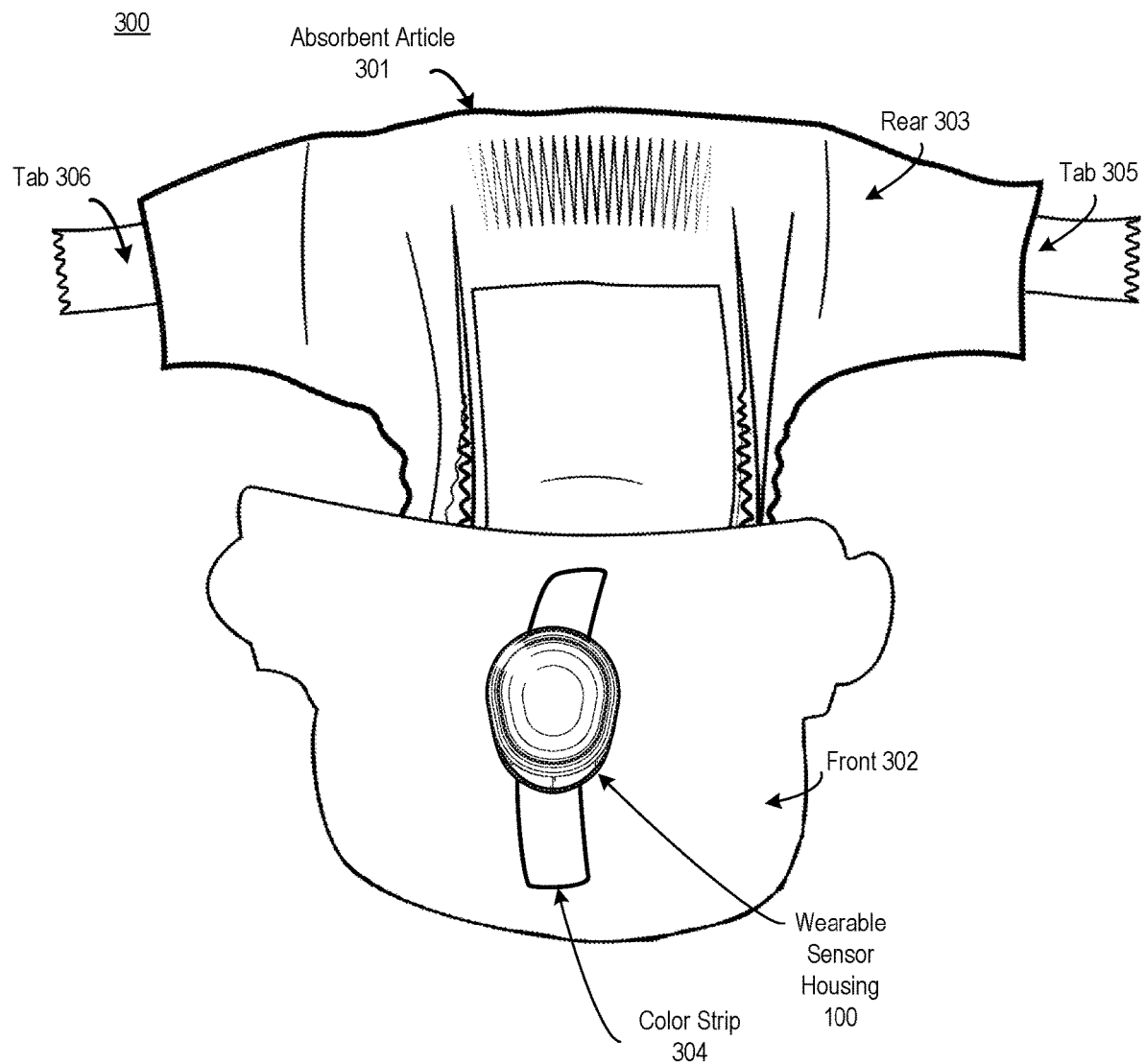
FIG. 3 depicts an exemplary placement of the wearable sensor enclosure of FIG. 1, in accordance with an aspect of the present disclosure.

In another example, the wearable sensor enclosure can include a superior end and an inferior end that are opposite to each other. FIG. 2 illustrates a wearable sensor enclosure with a superior end and an inferior end. FIG. 3 depicts an example of a placement of the wearable sensor enclosure on an absorbent article.

Figure 4:
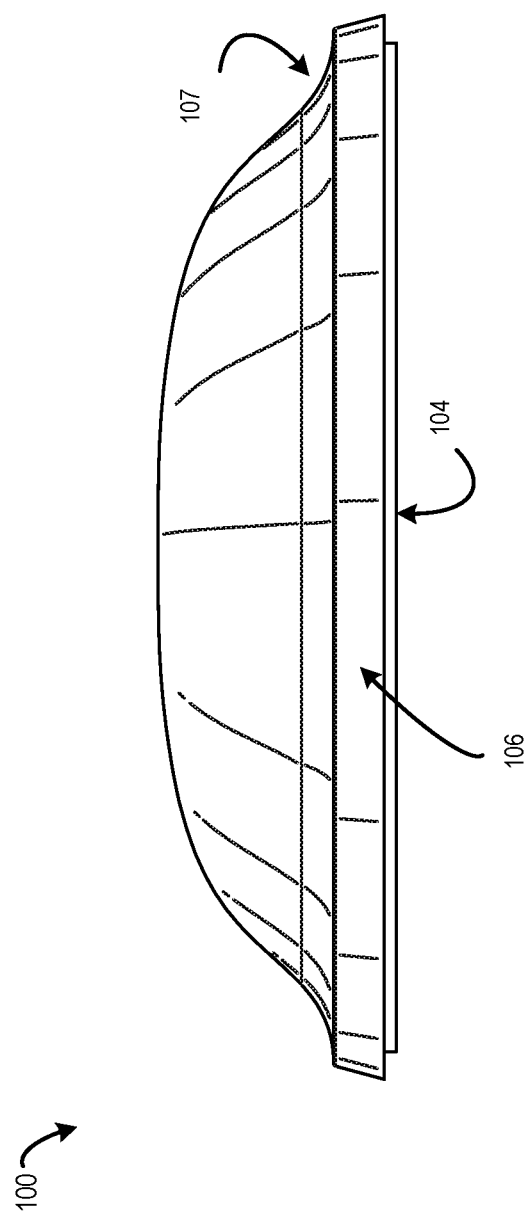
FIG. 4 depicts a view of the superior end of the wearable sensor enclosure of FIG. 1 from the perspective of the superior end, in accordance with an aspect of the present disclosure.
Figure 5:
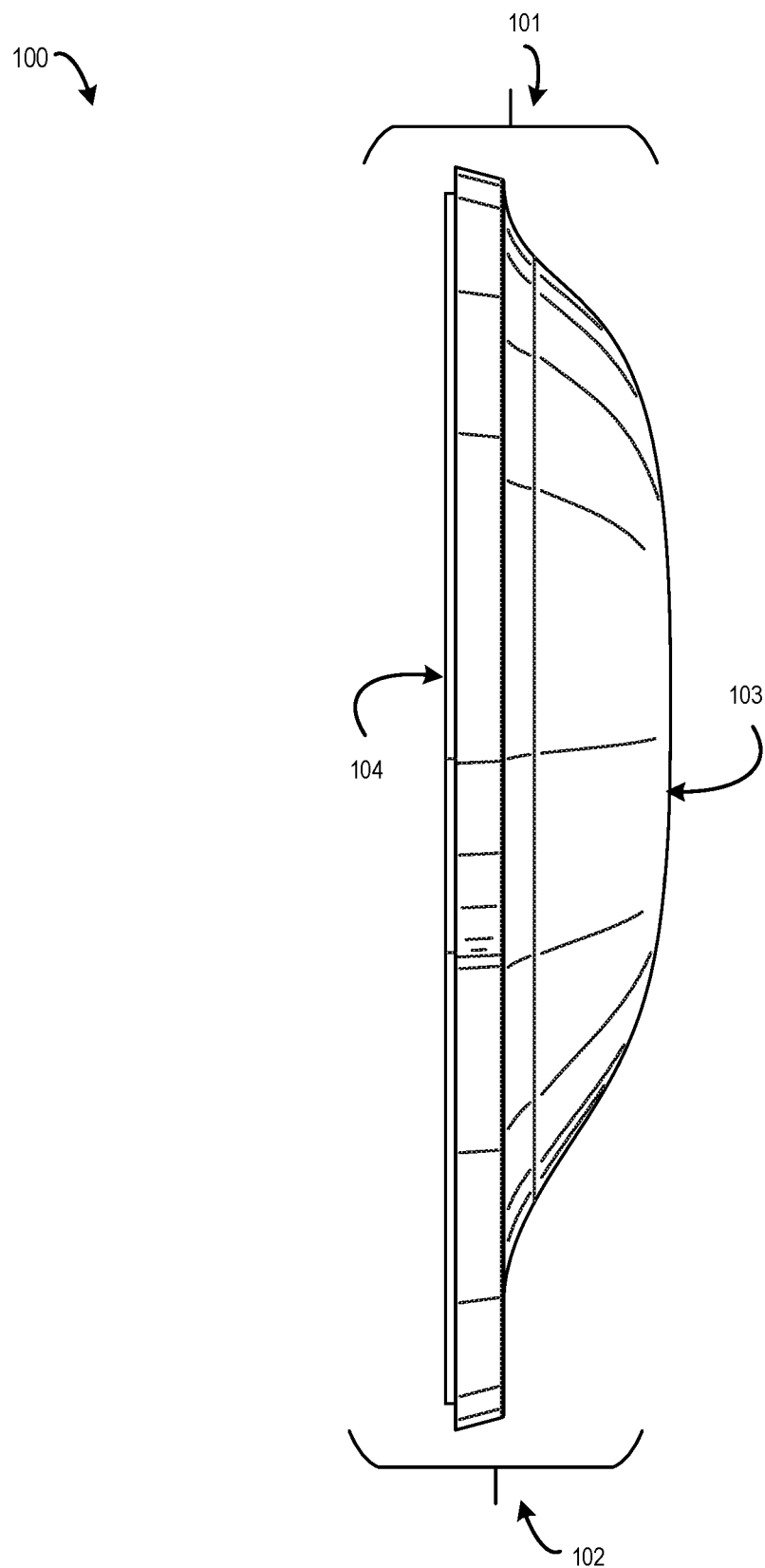
FIG. 5 depicts a side left view of the wearable sensor enclosure of FIG. 1, in accordance with an aspect of the present disclosure.

Referring now to FIGS. 4 and 5, the assembled wearable sensor enclosure 100 is shown in front and side views. In other words, the distal component 103 and proximal component 104 are nested or otherwise secured to one another. As shown, the protrusion 105 of the distal component 103 can protrude upwards as to facilitate space for internal devices or sensors. In contrast, as shown in FIG. 5, the outer lip 106 is narrow, having no electronic devices therein. A transition section 107 exists between the protrusion 105 and the outer lip 106. The transition section 107 can form a concave curve. In some cases, the presence of outer lip 106 can facilitate air flow around the wearable sensor enclosure 100, or the shape of this curve can create a channel of air in the event that the wearable sensor enclosure 100 is attempted to be swallowed or otherwise stuck with in an airway. This difference in shape between protrusion 105 and outer lip 106 can therefore provide an enhanced safety feature by minimizing a risk of choking in an event that an infant removes the enclosure and places it in his or her mouth.

Wearable sensor enclosure 100 can support any electronic devices housed within. For example, a printed circuit board (PCB) including a battery, sensor, antenna, processor, etc., can be placed between distal component 103 and proximal component 104. A PCB can be mounted on distal component 103, on proximal component 104, or in between. Examples are discussed further with respect to FIGS. 8-9.

Different materials can be used for components of the wearable sensor. Such materials used can be hard (e.g., hold their shape) or soft (e.g., malleable). Examples of materials include plastic, elastomer, or rubber. In one example, the outer lip 106 is made of a hard material with an additional soft material covering the hard material. This layering of materials can help provide wearable sensor enclosure 100 with a softer feel while maintaining an internal structure to protect internal components.

In some cases, the proximal component 104 can include an adhesive or an attachment device that can adhere proximal component 104, and thereby the wearable, to a wearer or an absorbent article. Examples of attachment devices include hooks and loops, buttons, snaps, adhesive stickers, or any combination thereof. In other cases, the proximal component 104 can attach to an adhesive surface.

In an example, the distal component 103 may contain a flexible outer material and an inner, hard material such as polycarbonate or triton. The inner material can help form a cavity within which the electronic devices are housed, hence causing a protruding area that helps define the protrusion 105. In another aspect, distal component 103 and/or proximal component 104 can be made of a rigid material to protect any electronic devices present inside the wearable sensor enclosure 100.

Examples of electronic devices that can be placed within the wearable sensor enclosure 100 include an accelerometer, gyroscope, an optical sensor, moisture sensor, sound emitting device, a temperature sensor, or any combination thereof. Additionally, the protrusion 105 can provide sufficient room for a printed circuit board that can include a battery, processor, integrated circuit, Light Emitting Diode (LED), or other components or any combination thereof.

In another aspect, the wearable sensor enclosure 100 includes a button area on the protrusion 105. The button area can be created by forming protrusion 105, at least in part, of a flexible material that can respond to movement. The button area can be any shape, for example, circular, square, or rectangular. In some cases, the one or more buttons can cause a device or switch inside the enclosure to be activated, which in turn can turn the electronic devices on or off. For example, a top of the distal component 103 can be made from a flexible material that can transmit a user's push or touch to a button or sensor located below, which in turn can open or close an electronic circuit, causing an action to be performed. Additionally, a transparent or partially transparent portion of the wearable sensor enclosure 100 can facilitate emitted light. Emitted light can indicate a status of the sensor to a user, e.g., whether the sensor is on or off, or is operating correctly.

Openings 110-111 (or sensor windows) facilitate light entering into or exiting from the wearable sensor enclosure 100. For example, an optical sensor can receive light through one or more of openings 110-111. In another example, an optical transmitter can transmit light through one or more of openings 110-111. Emitted light can be useful for detecting color of an object, e.g., color strip in a diaper, below the sensor. For example, a light source can emit a light and detect a measurement of received light. From the received light, a processor can determine a measure or volume of bodily exudate present in a diaper. In yet another example, a humidity or volatile organic compound (VOC) sensor can analyze air that flows through one or more of openings 110-111. Although two openings are shown, it should be understood that a single window or more than two windows may be provided. The windows may be formed as openings in the proximal component 104 that are overlaid with a transparent plastic, tempered glass, sealant, or any other material that will maintain watertight integrity of the wearable sensor enclosure 100 while also transmitting light wavelengths.

FIG. 2 depicts a top view of the wearable sensor enclosure of FIG. 1, in accordance with an aspect of the present disclosure. More specifically, FIG. 2 depicts the wearable sensor enclosure 100, superior end 101, inferior end 102, protrusion 105, and outer lip 106. As depicted, lines indicate a concavity formed between outer lip 106 and protrusion 105, as protrusion 105 can protrude outward from outer lip 106.

In some cases, the wearable sensor enclosure 100 can be oriented such that the superior end 101, a wider end, is the top end and the inferior end 102, a narrower end, is the bottom end. The narrower end can therefore provide a visual cue to orient the wearable sensor enclosure 100 such that the inferior end 102 is downward, e.g., towards an infant's legs, such that the superior end 101 is pointed upwards, e.g., towards an infant's belly button. In this manner, any internal sensors are correctly oriented with the wearer (e.g., vertically or horizontally). The narrower end can also provide a visual cue as to where the internal sensors lie inside wearable sensor enclosure 100 such that the sensors may be oriented over the color strip.

FIG. 3 depicts an exemplary placement of the wearable sensor enclosure of FIG. 1, in accordance with an aspect of the present disclosure. FIG. 3 depicts wearable sensor environment 300, which includes absorbent article 301 and wearable sensor enclosure 100. The absorbent article 301 may be an infant diaper, child training pants, an incontinence diaper or brief (such as the type worn by a patient in a hospital or nursing home), a feminine article, a patient bandage or wrap, or any other appropriate article. Absorbent article 301 includes front 302, rear 303, color strip 304, and tabs 305, 306. Tabs 305 and 306 can be an adhesive material that attach to absorbent article 301. Absorbent article 301 is configured to receive tabs 305 and 306, which keep the absorbent article 301 from slipping off a wearer.

Color strip 304 can be a color changing indicator that indicates a presence or volume of bodily exudate in absorbent article 301. Color changing indicators are designed to change color in response to contact with a substance having a particular property, such as a pH level. Examples include be Bromocresol green, which changes color based on the pH of a liquid to which the color changing indicator has been exposed. Other color changing indicators can be used. The detected pH level can be correlated with a volume of bodily exudate, because the pH level changes as the volume of bodily exudate in the absorbent article changes.

Accordingly, wearable sensor enclosure 100 can be placed on absorbent article 301, for example, over color strip 304, such that wearable sensor enclosure 100 can detect a change in color strip 304. Other exemplary placements include the front 302, side, or rear 303 of the absorbent article 301. As depicted, wearable sensor enclosure 100 is oriented such that the superior end 101 is pointed upwards towards a belly button or chest of the infant wearing absorbent article 301, and the inferior end 102 is pointed downwards.

As discussed above in connection FIG. 1, wearable sensor enclosure 100 can include one or more sensors. For example, if the one or more sensors include an accelerometer, when the wearable sensor enclosure 100 is placed on absorbent article 301, the wearable sensor enclosure 100 can sense movement by the wearer of the absorbent article 301 or of the absorbent article 301 itself. If the one or more sensors include an optical sensor, the wearable sensor enclosure 100 can emit a light source onto absorbent article 301 and measure an amount or color of light reflected from absorbent article 301. Such measurements can then be used to determine a presence, absence, or volume of moisture or bodily exudate such as blood, urine, or feces present in absorbent article 301.

In some cases, the outer lip 106 varies in width. For example, a first distance can be measured from the perimeter of wearable sensor enclosure 100 to the protrusion 105 as measured at the superior end 101. A second distance can be measured from the perimeter to the protrusion 105 at the inferior end 102. When the first distance, e.g., at the inferior end 102, is longer than the second distance, e.g., at the superior end 101, the preferred orientation of the sensor is made clearer.

FIG. 4 depicts a view of the superior end of the wearable sensor enclosure of FIG. 1 from the perspective of the superior end, in accordance with an aspect of the present disclosure. FIG. 4 depicts the wearable sensor enclosure 100, distal component 103, proximal component 104, and outer lip 106. As depicted, lines indicate a concave curve between distal component 103 and proximal component 104, through the transition 107. In this manner, the transition 107 and/or the outer lip 106 create a ridge, edge, or outer flange. Examples of radii of curvature for the concave curve are 1-15 mm. Other radii are possible.

FIG. 5 depicts a side left view of the wearable sensor enclosure of FIG. 1. FIG. 5 depicts the wearable sensor enclosure 100, superior end 101, inferior end 102, distal component 103, and proximal component 104.

Figure 6:
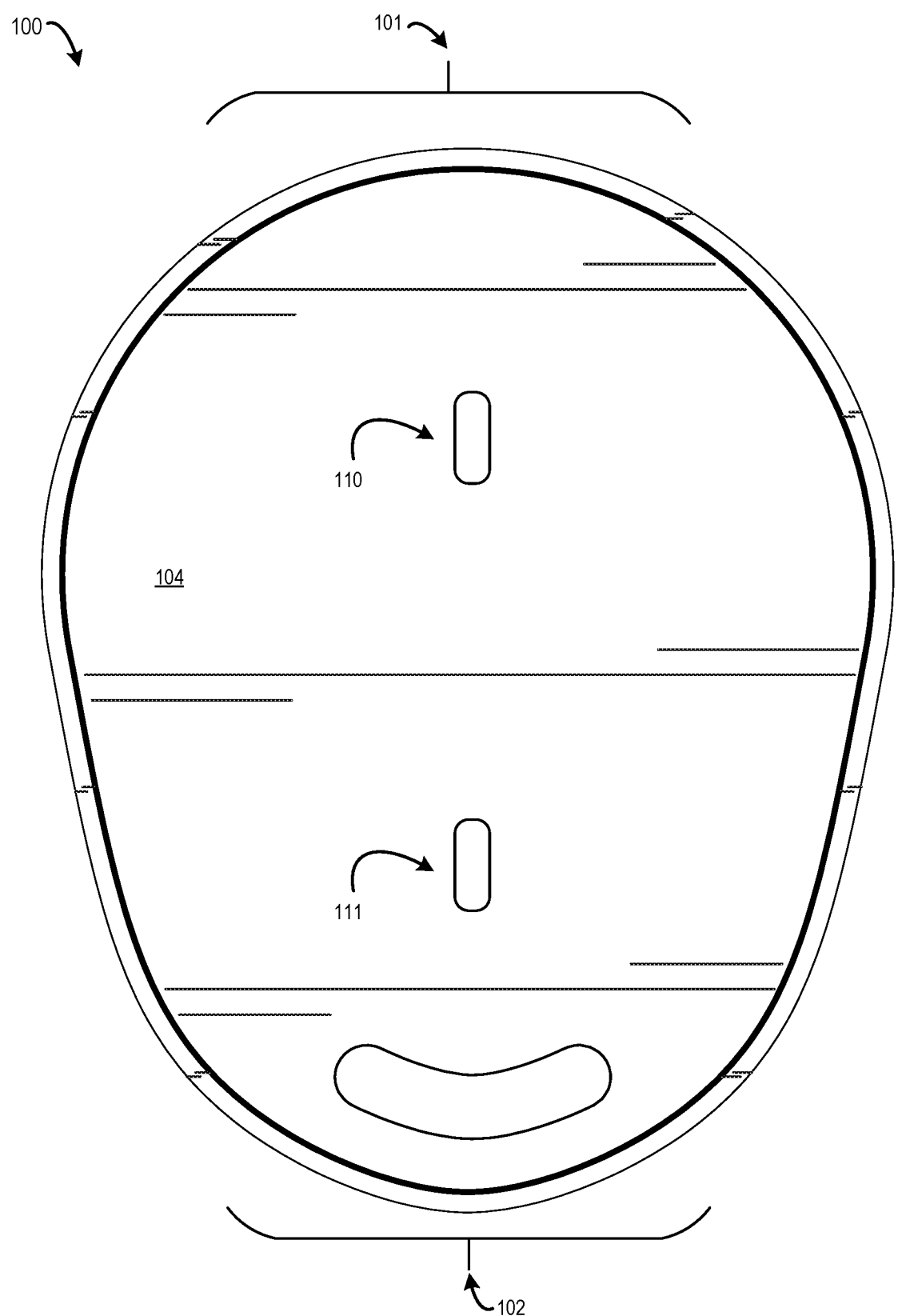
FIG. 6 depicts a bottom view of the wearable sensor enclosure of FIG. 1, in accordance with an aspect of the present disclosure.

FIG. 6 depicts a bottom view of the wearable sensor enclosure of FIG. 1. FIG. 6 depicts the wearable sensor enclosure 100, superior end 101, inferior end 102, and proximal component 104.

Figure 7:
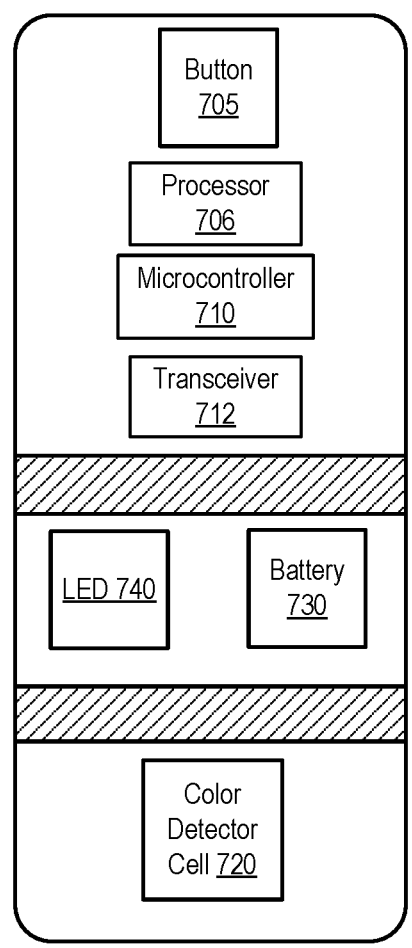
FIG. 7 depicts examples of electronic devices which can be placed inside the wearable sensor enclosure of FIG. 1, in accordance with an aspect of the present disclosure.

FIG. 7 depicts examples of electronic devices which can be placed inside the wearable sensor enclosure 100 of FIG. 1. FIG. 7 depicts sensor system 700, which includes one or more of button 705, processor 706, microcontroller 710, transceiver 712, Light Emitting Diode (LED) 740, battery 730, and color detector cell 720, or any combination thereof.

Processor 706 is a device that can process a measured quantity of light and optionally remove a measurement of ambient light therefrom. Processor 706 can be an analog device or a digital device such as a processor. Examples of processors include general purpose processors, controllers, and signal processors.

Microcontroller 710 is configurable to control color detector cell 720 or other sensors such as volatile organic compound (VOC) sensors, accelerometers, gyroscopes, or humidity sensors. Examples of microcontrollers include general purpose processors, controllers, signal processors, and application-specific integrated circuits (ASICs).

Transceiver 712 is configurable to send or receive wireless communications over protocols such as WiFi® or Bluetooth®. Sensor system 700 may also include a switch, electrical connectors, a volatile organic compound ("VOC") sensor, a temperature sensor, a humidity sensor, an ambient light sensor.

Sensor system 700 can include one or more color detector cells 720. Color detector cell 720 includes a light source such as an LED 740 and a photodetector such as a photodiode. Color detector cell 720 can transmit light or receive reflected light through one or more of openings 110-111.

In an example, a color sensing application operating on microcontroller 710 causes LED 740 to emit a light on a color changing indicator in absorbent article 301. Color detector cell 720 then measures an amount of received light reflected from the color changing indicator. Using the measurement, processor 706 disambiguates a contribution of ambient light and passes a measurement of the color of the light to microcontroller 710. Microcontroller 710 determines, based on the color of the light, a presence and volume of bodily exudate present in the absorbent article.

In some cases, multiple color detector cells can be used. A presence of multiple color detector cells enables a calculation of multiple data points to more accurately estimate a total volume of bodily exudate present. Color detector cell detects light reflected by an object such as a color changing indicator in absorbent article 301, such as ambient light or pulsed light from the light source(s). The output of color detector cell 720 is provided to processor 706. The output of processor 706 can be provided to microcontroller 710.

In some cases, battery 730 can be disposable with an exemplary life of three to six months, removing the need for a charging system. In other cases, battery 730 can be rechargeable.

In addition, sensor system 700 can cause an alarm, such as an audible beep, based on a threshold level of bodily exudate being detected. Accordingly, sensor system 700 can include a speaker or other audio output device. Sensor system 700 can also cause a transmission of an alert to another device, for example, operated by a caretaker. Sensor system 700 can include a transmitter or transceiver capable of transmitting a radio signal to an external device. A color sensing application operating on a microcontroller installed within wearable sensor enclosure 100 can also log events, such as when bodily exudate is detected, to memory. Wearable sensor enclosure 100 can transmit measurements to an external device such as to a mobile phone operated by a caregiver.

Sensor system 700 can include a switch to activate or deactivate the sensor system 700. The switch can be any suitable switch, such as a momentary switch or on/off switch. The switch can cause power to be connected from the battery 730 to the electronic devices in sensor system 700 and the color detector cell 720. Alternatively, the switch can provide an input to processor 706 to cause processor 706 to take an action. Sensor system 700 can include one or more electrical connectors, which can be used to debug the sensor system 700, calibrate the sensor system 700, reset the sensor system 700 to factory settings, upgrade software on the sensor system 700, etc.

In an aspect, sensor system 700 can also include a temperature sensor, which can detect heat from substances such as bodily exudate. In conjunction with data obtained from color detector cell 720, the temperature sensor can provide additional information such as a temporary increase in temperature to microcontroller 710. In another aspect, sensor system 700 can also include a humidity sensor, which can detect the presence of humidity, e.g., from bodily exudate. In conjunction with data obtained from color detector cell 720, the humidity sensor can provide additional information such as a notification of a temporary increase in humidity to microcontroller 710.

Figure 8:
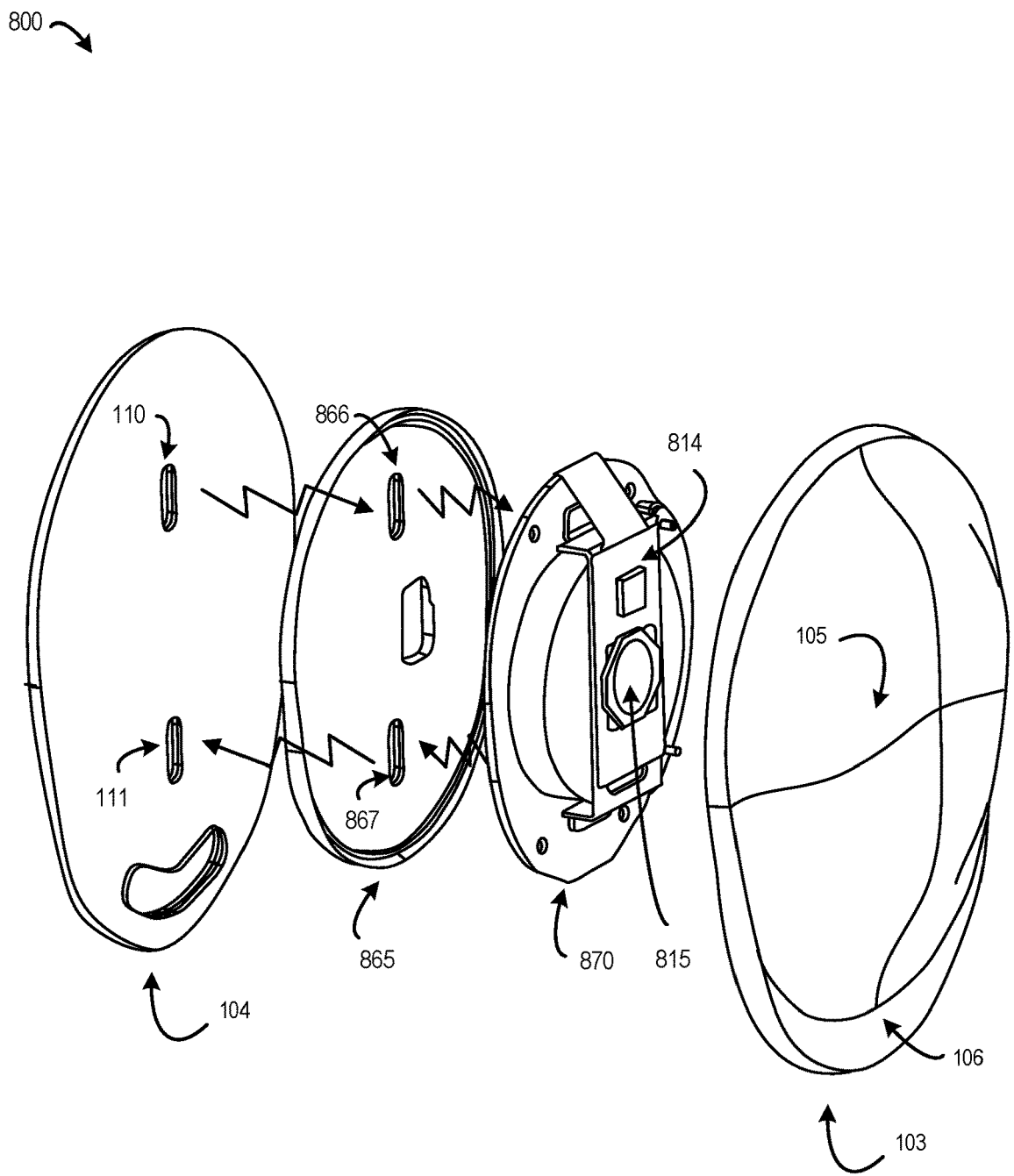
FIG. 8 depicts an embodiment of a wearable sensor enclosure that is configured to house electronic devices, in accordance with an aspect of the present disclosure.

FIG. 8 depicts an embodiment of a wearable sensor enclosure that is configured to house electronic devices in accordance with an aspect of the present disclosure. FIG. 8 depicts wearable sensor housing 800, which includes distal component 103, proximal component 104, circuit board 870, and circuit board backing 865.

Proximal component 104 can be integrated with or separate from circuit board backing 865. Proximal component 104 includes openings 110-111, which can allow light to pass through. Proximal component 104 can provide support to distal component 103 and circuit board 870.

Circuit board 870 can include electronic devices 814, button 815, and a color detector cell (not depicted), light source (not depicted). An example of color detector cell is color detector cell 720. An example of light source is LED 740. Electronic devices 814 can include any suitable electronic devices for sensing such as processor 706, microcontroller 710, etc. Circuit board 870 can be inserted directly into distal component 103.

Circuit board backing 865 can provide support to circuit board 870. In some cases, circuit board backing 865 can have a translucent portion or one or more openings 866 and 867 to allow light to pass through. Openings 866-867 can line up with a color detector cell and/or a light source located on circuit board 870, and with openings 110-111 located on proximal component 104.

Distal component 103 can include an exterior button (not depicted) that can be configured to receive input from a user such as a mechanical push. The exterior button can be an area of over-molded elastomer without rigid lower support. A push translates into movement. In turn, the movement causes pressure to be applied to button 815, which can cause one or more operations to be performed by electronic devices 814 such as activating or deactivating sensors, etc. In this manner, force from a user's finger translates to button 815. Button 815 can any mechanical device that causes electrical contacts to be formed and/or broken such as a push-button switch, on-off switch, etc.

Distal component 103 can be made of a rigid material or a combination of rigid material and an elastomer. Wearable sensor housing 800 can include joints or seams between components can be sealed with an adhesive or otherwise molded together. For example, a weld located between the distal component 103 and the proximal component can ensure that liquids do not easily enter wearable sensor housing 800. For example, this weld can result in a water-tight factory seal. Batteries or other power devices may be single use, such that the end user does not need to replace batteries. Instead, the batteries or other power devices are sealed into the device.

In another aspect, the wearable sensor housing 800 includes an interior sensor enclosure. The interior sensor enclosure can include one or more openings to allow light to pass through, such as for a photodetector or from a LED. When present, these openings can be configured to line up with openings 110-111 and openings 866-867. The interior sensor enclosure can be fabricated with a rigid material, for example, to better protect any electronic devices or sensors that are present within.

Figure 9:
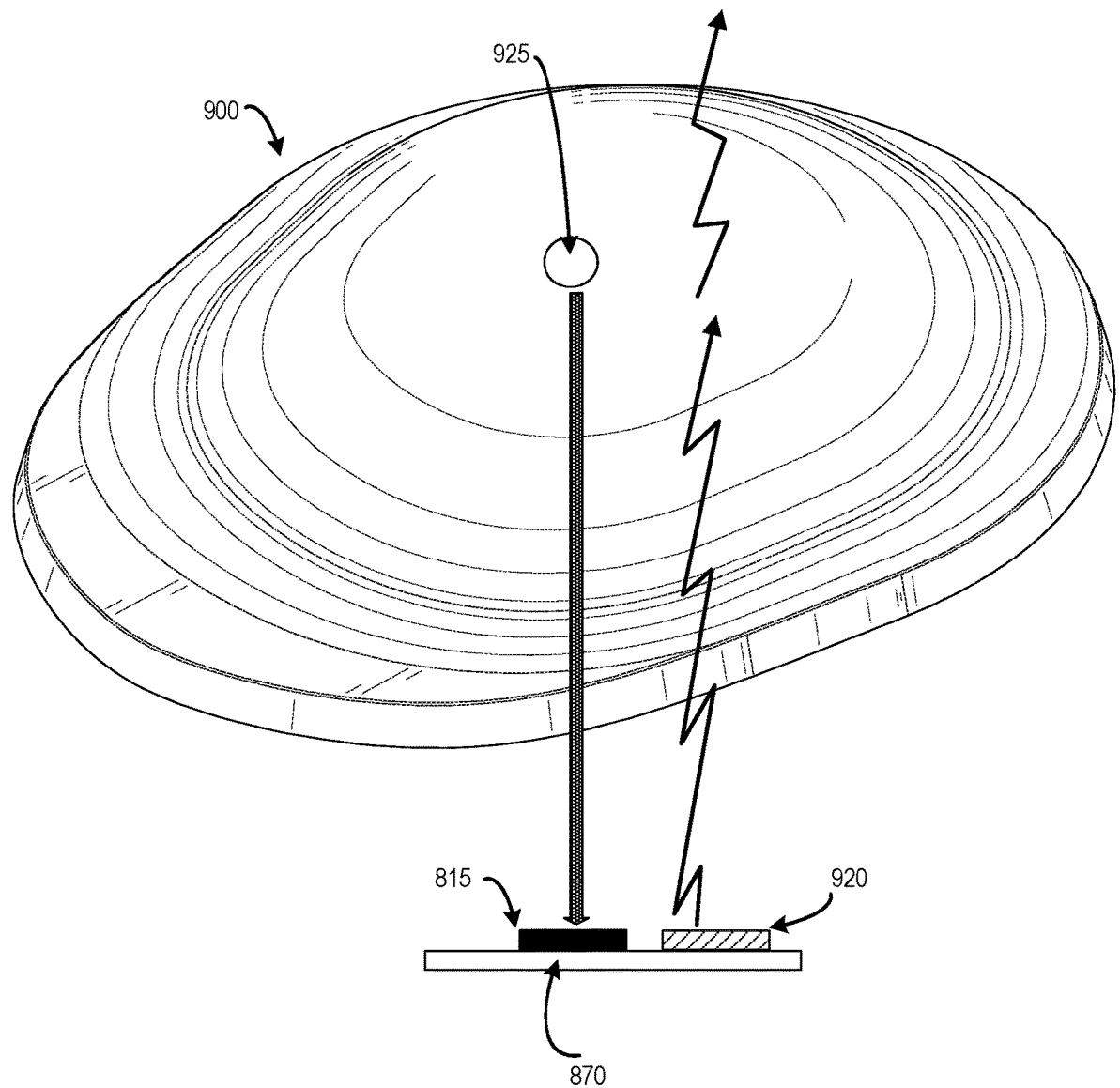
FIG. 9 depicts an aspect of a wearable sensor enclosure with a modified inner portion to facilitate interactions and an indicator light, in accordance with an aspect of the present disclosure.

FIG. 9 depicts an aspect of a wearable sensor enclosure with a modified inner portion to facilitate interactions and an indicator light, in accordance with an aspect of the present disclosure. FIG. 9 includes wearable sensor enclosure 900. Wearable sensor enclosure 900 includes button area 925 and circuit board 870.

Circuit board 870 includes button 815 and LED 920. As shown, and as described with respect to FIG. 8, pressing button area 925 causes button 815 to be activated. Additionally or alternatively, LED 920 can output light through the surface of wearable sensor enclosure 900. In this manner, a user can receive feedback, for example, whether the sensor is operating correctly. LED 920 can emit light of any color, e.g., white, blue, yellow, red, or green. Additionally, LED 920 can be configured to emit a different color of light based on a status. Examples of status include correct operation, incorrect operation, correct alignment, incorrect alignment, and low battery.

Figure 10:
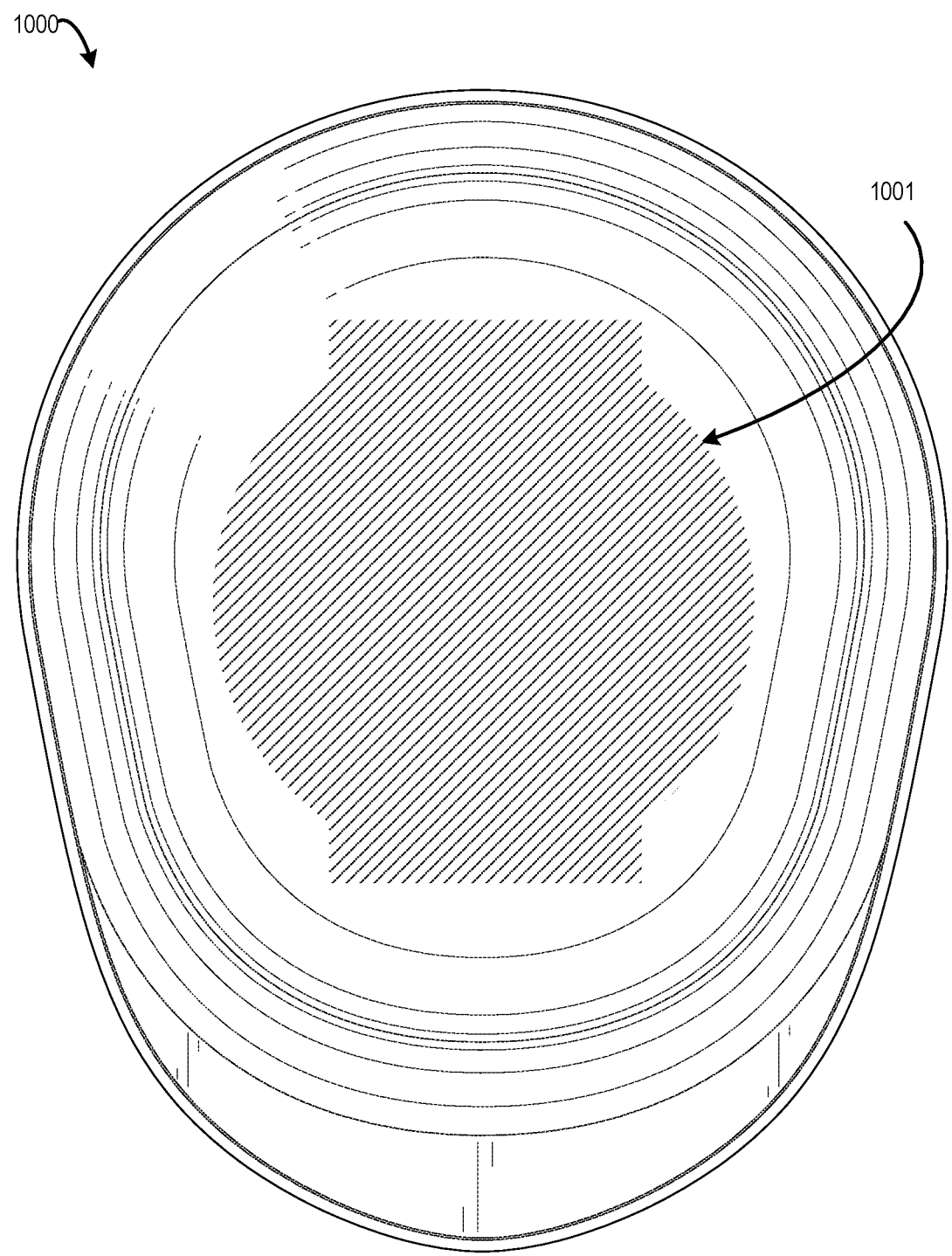
FIG. 10 depicts a top view of the wearable sensor enclosure of FIG. 9, in accordance with an aspect of the present disclosure.

FIG. 10 depicts a top view of the wearable sensor enclosure of FIG. 9. FIG. 10 shows a wearable sensor enclosure 1000 that has a cutout portion 1001. Cutout portion 1001 can be an area of a more rigid material that is removed. A more flexible material may be placed on or under cutout portion 1001. The more flexible material is illustrated in FIG. 10 by diagonal hashmarks. Providing this more flexible material can permit operation of a button (e.g., button area 925), while maintaining an otherwise rigid structure.

For example, wearable sensor enclosure 1000 may be made of a rigid material. A second part of material covering cutout portion 1001 may be manufactured of an elastomeric material. In this way, certain parts of the wearable sensor enclosure 100 can be flexible. Additionally, use of an elastomer can avoid a need for separate sealing methods to prevent water or liquids from easily entering the wearable sensor enclosure.

Numerous specific details are set forth herein to provide a thorough understanding of the claimed subject matter. However, those skilled in the art will understand that the claimed subject matter may be practiced without these specific details. In other instances, methods, apparatuses, or systems that would be known by one of ordinary skill have not been described in detail so as not to obscure claimed subject matter.

Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provide a result conditioned on one or more inputs. Suitable computing devices include multi-purpose microprocessor-based computer systems accessing stored software that programs or configures the computing system from a general purpose computing apparatus to a specialized computing apparatus implementing one or more aspects of the present subject matter. Any suitable programming, scripting, or other type of language or combinations of languages may be used to implement the teachings contained herein in software to be used in programming or configuring a computing device.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

That which is claimed is:

1. A wearable sensor enclosure comprising:
   a proximal component defining an opening; and
   a distal component attached to the proximal component and having a perimeter, the distal component comprising:
   a protrusion positioned in an interior of the distal component;
   an outer lip positioned along the perimeter and surrounding the protrusion, wherein the protrusion and the outer lip connect at a transition section that forms a concave curve to facilitate air flow around the wearable sensor enclosure; and
   an interior sensor enclosure located between the distal component and the proximal component, wherein the interior sensor enclosure comprises one or more of: (i) a light source configured to emit light through the opening, or (ii) a light sensor configured to receive light through the opening.

2. The wearable sensor enclosure of claim 1, wherein the protrusion further comprises one or more of (i) a button area configured to activate an electronic switch disposed within the wearable sensor enclosure or (ii) an additional light source configured to emit light through the protrusion.

3. The wearable sensor enclosure of claim 1, wherein the concave curve comprises a radius of 1-6 mm.

4. The wearable sensor enclosure of claim 1, wherein the wearable sensor enclosure is at least partially made from a flexible material and the proximal component comprises an adhesive or attachment device for attaching to a diaper.

5. The wearable sensor enclosure of claim 1, further comprising one or more of: an accelerometer, a gyroscope, a radio, a power source, a temperature sensor, a moisture sensor, or a sound emitting device.

6. The wearable sensor enclosure of claim 1, further comprising an orientation marking indicating a preferred orientation of the wearable sensor enclosure.

7. A wearable sensor enclosure comprising:
   a proximal component defining an opening; and
   a distal component attached to the proximal component and having a perimeter, the distal component comprising:
   a protrusion positioned in an interior of the distal component; and
   an outer lip positioned along the perimeter and surrounding the protrusion, wherein the protrusion and the outer lip connect at a transition section that forms a concave curve to facilitate air flow around the wearable sensor enclosure;
   a superior end located opposite an inferior end, wherein the superior end has a first width and the inferior end has a second width, wherein the second width is less than the first width; and
   an interior sensor enclosure located between the distal component and the proximal component, wherein the interior sensor enclosure comprises one or more of: (i) a light source configured to emit light through the opening, or (ii) a light sensor configured to receive light through the opening.

8. The wearable sensor enclosure of claim 7, further comprising an orientation marking, the orientation marking indicating a preferred orientation of the wearable sensor enclosure.

9. The wearable sensor enclosure of claim 8, further comprising a sensor having a preferred orientation, wherein the sensor is correctly oriented when the wearable sensor enclosure is oriented consistently with the preferred orientation indicated by the orientation marking.

10. The wearable sensor enclosure of claim 7, further comprising (i) a first distance from the perimeter and the protrusion as measured at the superior end and (ii) a second distance from the perimeter and the protrusion as measured at the inferior end, wherein the first distance and the second distance are different.

11. The wearable sensor enclosure of claim 7, wherein the protrusion further comprises one or more of (i) a button area configured to receive a push and activate an electronic switch disposed within the wearable sensor enclosure or (ii) an additional light source configured to emit light through the protrusion.

12. The wearable sensor enclosure of claim 7, wherein the wearable sensor enclosure is at least partially made from a flexible material.

13. The wearable sensor enclosure of claim 7, wherein the proximal component comprises an adhesive or attachment device for attaching to a diaper.

14. The wearable sensor enclosure of claim 7, further comprising one or more of: an accelerometer, a gyroscope, a radio, a power source, a temperature sensor, a moisture sensor, or a sound emitting device.

15. The wearable sensor enclosure of claim 7, wherein the concave curve comprises a radius of 1-6 mm.

16. A wearable sensor enclosure comprising:
    a proximal component defining an opening; and
    a distal component attached to the proximal component and having a perimeter, the distal component comprising:
    a protrusion positioned in an interior of the distal component and comprising a button area that is configured to activate an electronic switch within the wearable sensor enclosure;
    an outer lip positioned along the perimeter and surrounding the protrusion, wherein the protrusion and the outer lip connect at a transition section that forms a concave curve to facilitate air flow around the wearable sensor enclosure; and
    an interior sensor enclosure located between the distal component and the proximal component, wherein the interior sensor enclosure comprises one or more of: (i) a light source configured to emit light through the opening, or (ii) a light sensor configured to receive light through the opening.

17. The wearable sensor enclosure of claim 16, further comprising a superior end located opposite an inferior end, wherein the superior end has a first width and the inferior end has a second width, wherein the second width is less than the first width.

18. The wearable sensor enclosure of claim 16, further comprising an orientation marking on the protrusion, the orientation marking indicating a preferred orientation of the wearable sensor enclosure.

19. The wearable sensor enclosure of claim 16, further comprising one or more of: an accelerometer, a gyroscope, a radio, a power source, a temperature sensor, a moisture sensor, or a sound emitting device.

20. The wearable sensor enclosure of claim 16, wherein the concave curve comprises a radius of 1-6 mm.

\* \* \* \* \*